(12) United States Patent
Horvath et al.

(10) Patent No.: US 7,582,743 B2
(45) Date of Patent: Sep. 1, 2009

(54) TEXTURIZING LACTIC BACTERIA

(75) Inventors: Philippe Horvath, Scorbe-Clairvaux (FR); Elise Manoury, Chatellerault (FR); Sonia Huppert, Vincennes (FR); Christophe Fremaux, Poitiers (FR)

(73) Assignee: Danisco France, Paris (FR)

( * ) Notice: Subject to any disclaimer, the term of this patent is extended or adjusted under 35 U.S.C. 154(b) by 149 days.

(21) Appl. No.: 10/548,940

(22) PCT Filed: Mar. 12, 2004

(86) PCT No.: PCT/FR2004/000610

§ 371 (c)(1),
(2), (4) Date: Feb. 7, 2006

(87) PCT Pub. No.: WO2004/085607

PCT Pub. Date: Oct. 7, 2004

(65) Prior Publication Data

US 2006/0240539 A1   Oct. 26, 2006

(30) Foreign Application Priority Data

Mar. 17, 2003  (FR) .................. 03 03242

(51) Int. Cl.
*C12N 1/20* (2006.01)
*C12N 15/00* (2006.01)
*C07H 21/04* (2006.01)

(52) U.S. Cl. ............... 536/23.7; 435/252.3; 435/320.1
(58) Field of Classification Search ............. 536/23.7; 435/252.3, 320.1

See application file for complete search history.

(56) References Cited

U.S. PATENT DOCUMENTS 5,733,765 A * 3/1998 Mollet et al. ............. 435/183

FOREIGN PATENT DOCUMENTS

WO   WO 0179500 A   10/2001

OTHER PUBLICATIONS

Broadbent, J.R., et al., Biochemistry, genetics, and applications of exopolysaccharide production in *Streptococcus thermophilus*: a review, J. Dairy Sci. (Feb. 2003) 86:407-423, American Dairy Science Association, XP009018436.
Pluvinet, A., *Streptococcus thermophilus* eps locus (Jan. 4, 2002), XP-002256424.
Guedon, G, et al., *Streptococcus thermophilus* variable locus including exopolysaccharide synthesis genes and insertion sequences (Aug. 3, 1999), XP-002256425.
Kneidinger, B, et al., *Aneurinibacillus thermoaerophilus* putative sugar transferase gene, partial cds (Apr. 2, 2001), XP-002256426.
Llull, D, et al., *Streptococcus pneumoniae* cap 37 locus (Oct. 21, 1999), XP-002256427.
Rallu, F., et al., *Streptococcus thermophilius* eps type VII operon and flanking sequence (Nov. 7, 2002), XP-002256428.
Rallu, F., et al., *Streptococcus thermophilius* eps10 operon #2 (Feb. 21, 2002), XP-002256429.
Ianelli, F., et al., *Streptococcus pneumoniae* DexB (dexb) gene, partial cds (Feb. 1, 1999), XP-002256430.

* cited by examiner

*Primary Examiner*—Mark Navarro
(74) *Attorney, Agent, or Firm*—Frost Brown Todd LLC

(57) ABSTRACT

The invention relates to a novel strain of lactic bacteria comprising at least one sequence selected from a group consisting of nucleotide sequences SEQ ID No. 1, SEQ ID No. 2, SEQ ID No. 3, SEQ ID No. 4, SEQ ID No. 5, SEQ ID No. 6, SEQ ID No. 7, SEQ ID No. 8 and to a method for the production of said strains. The invention also relates to the sequences SEQ ID Nos. 1-8 and to a nucleic acid, vectors and plasmids comprising said sequences. The invention further relates to food products, especially milk products containing said strains.

41 Claims, 4 Drawing Sheets

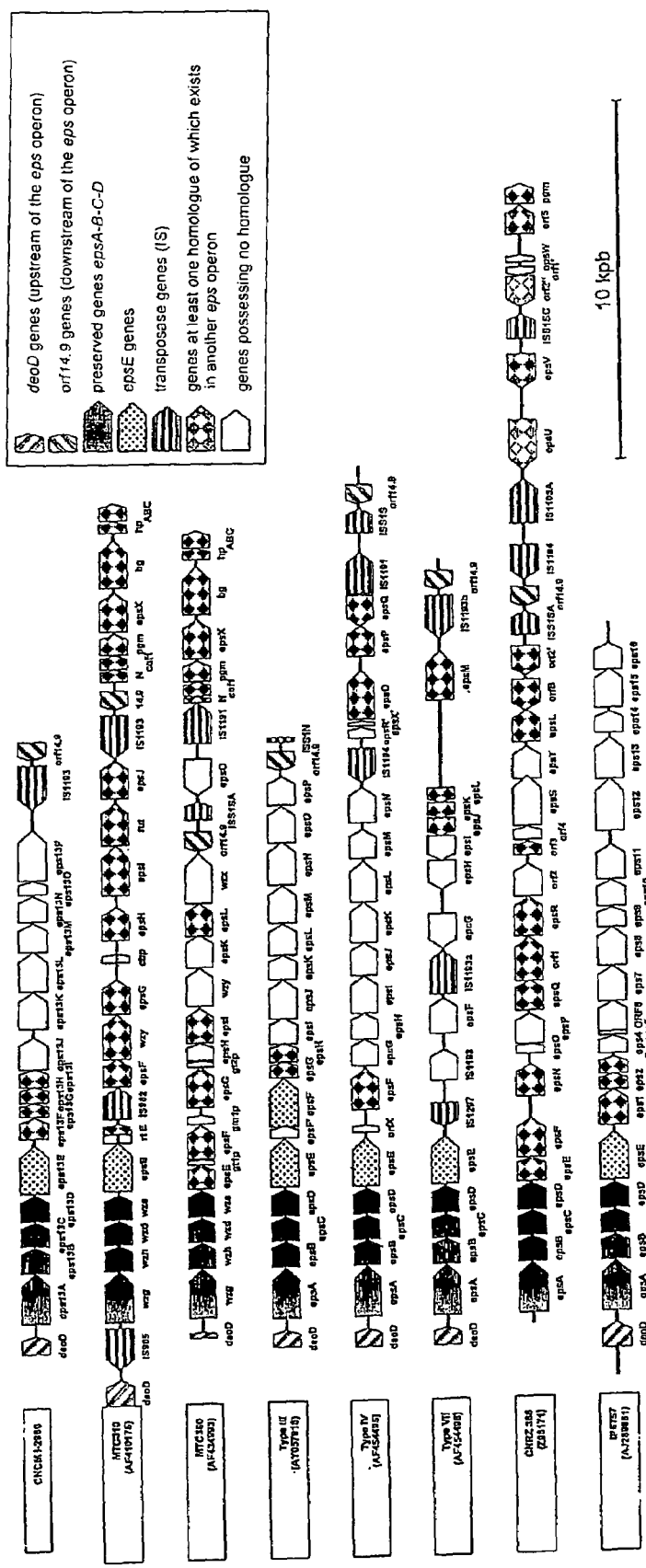
Figure 1: Genomic structure of PS operons of Streptococcus thermophilus

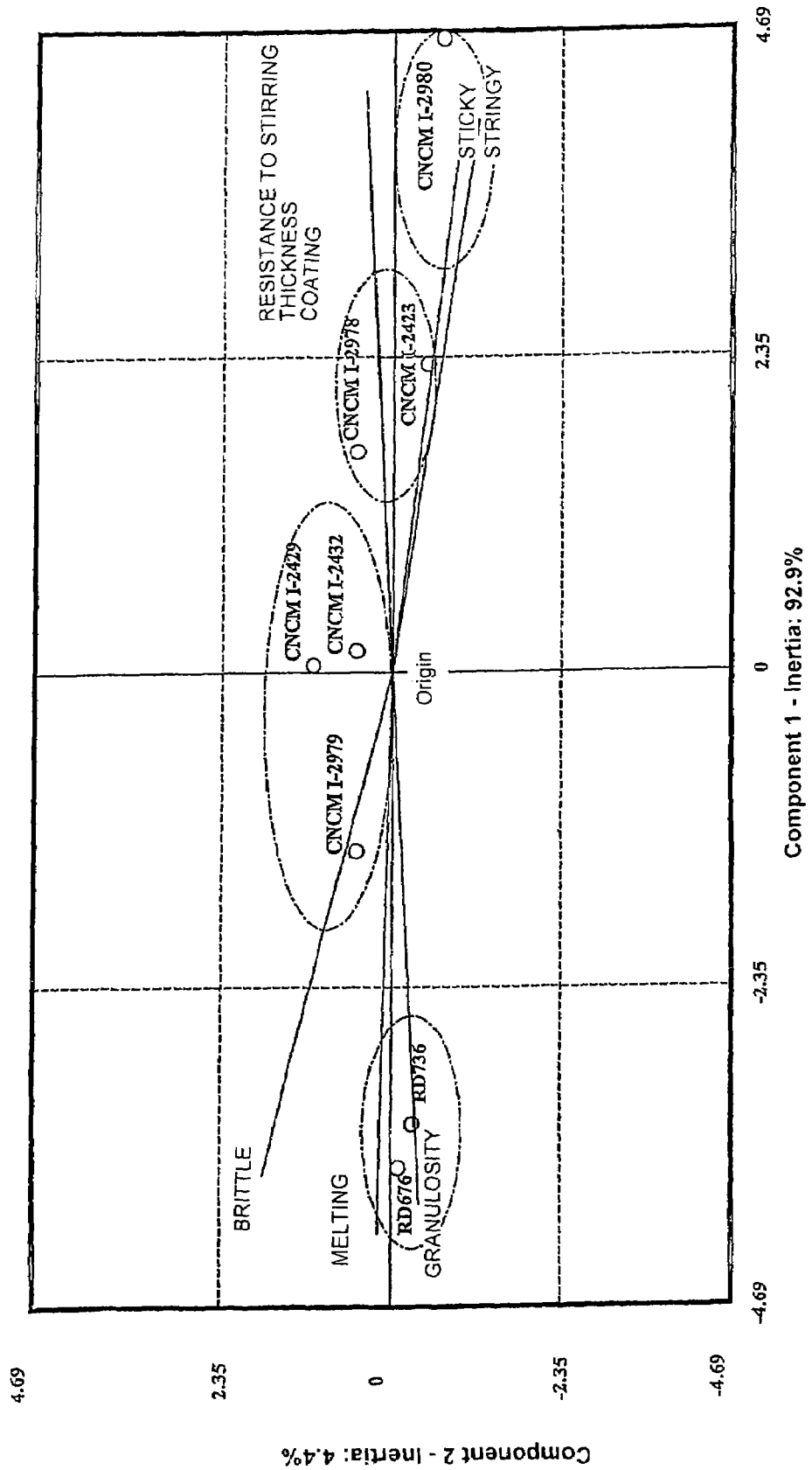
Figure 2: Graphical representation of the factorial design 1-2 of the PCA obtained from sensory data on fermented milks obtained with the different strains of the study.

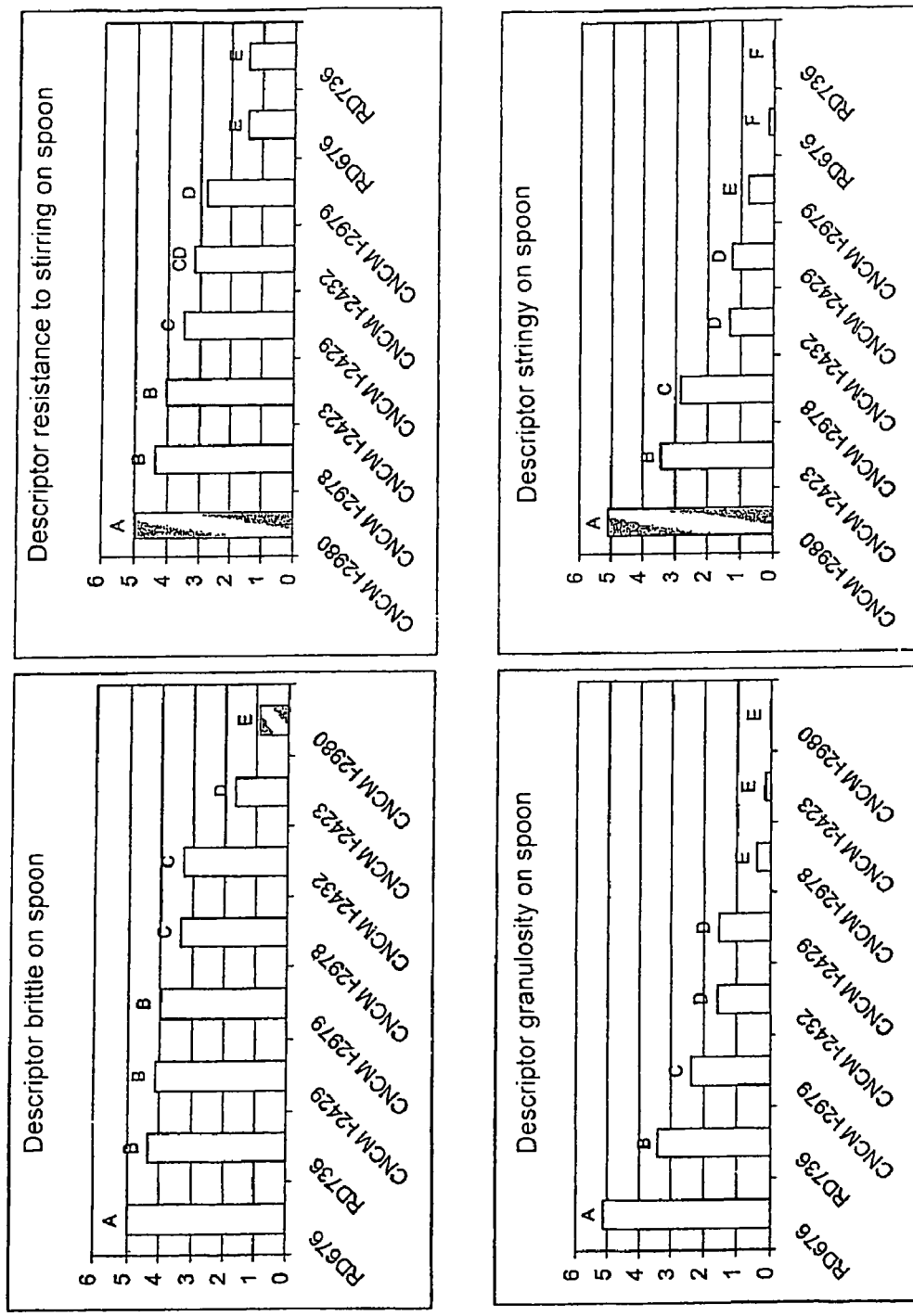
Figure 3: Graphical representations of the means of the scores obtained on the TEXTURE ON SPOON descriptors for each of the strains of the study. Interpretation of the results of the Newman-Keuls test: the difference between the strains connected by the same letter is not significant.

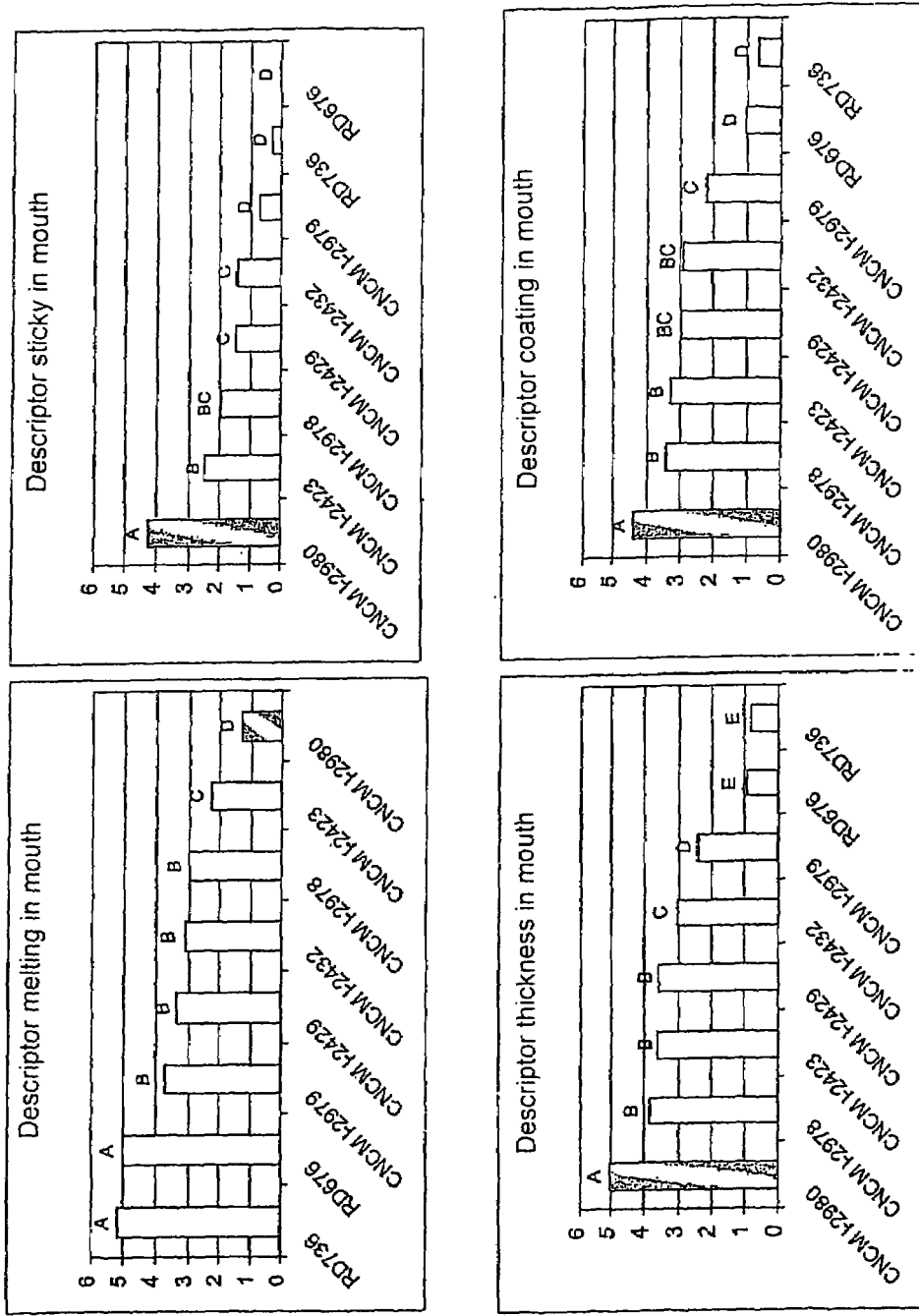
*Figure 4:* Graphical representations of the means of the scores obtained on the TEXTURE IN MOUTH descriptors for each of the strains of the study. Interpretation of the results of the Newman-Keuls test: the difference between the strains connected by the same letter is not significant.

TEXTURIZING LACTIC BACTERIA

A subject of the present invention is strains of lactic bacteria comprising at least one sequence selected from the group constituted by the nucleotide sequences SEQ ID No. 1, SEQ ID No. 2, SEQ ID No. 3, SEQ ID No. 4, SEQ ID No. 5, SEQ ID No. 6, SEQ ID No. 7, SEQ ID No. 8 as well as a process for constructing these strains. Finally, the invention relates to food products comprising and/or produced with said strains.

The food industry uses numerous bacteria, in the form in particular of ferments, in particular lactic bacteria, in order to improve the taste and the texture of foods but also in order to extend the shelf life of these foods. In the case of the dairy industry, lactic bacteria are used intensively in order to bring about the acidification of milk (by fermentation) but also in order to texturize the product into which they are incorporated.

Among the lactic bacteria used in the food industry, there can be mentioned the genera *Streptococcus, Lactococcus, Lactobacillus, Leuconostoc, Pediococcus* and *Bifidobacterium*.

The lactic bacteria of the species *Streptococcus thermophilus* are used extensively alone or in combination with other bacteria for the production of food products, in particular fermented products. They are used in particular in the formulation of the ferments used for the production of fermented milks, for example yogurts. Certain of them play a dominant role in the development of the texture of the fermented product. This characteristic is closely linked to the production of polysaccharides. Among the strains of *Streptococcus thermophilus* it is possible to distinguish texturizing and non-texturizing strains.

By texturizing strain of *Streptococcus thermophilus* is meant a strain which generates fermented milks having, under the conditions described as an example, a viscosity greater than approximately 35 Pa·s, a thixotropic area of less than approximately 2000 Pa/s and a yield point of less than approximately 14 Pa. A strain of *Streptococcus thermophilus* can be defined as strongly texturizing in that it generates fermented milks having, under the conditions described as an example, a viscosity greater than approximately 50 Pa·s, a thixotropic area of less than approximately 1000 Pa/s and a yield point of less than approximately 10 Pa.

In order to meet the requirements of the industry, it has become necessary to propose novel texturizing strains of lactic bacteria, in particular of *Streptococcus thermophilus*.

Thus the problem that the invention proposes to resolve is to provide a strain of lactic bacterium having good properties for texturizing food products.

For this purpose the invention proposes a strain of lactic bacterium which comprises at least one sequence selected from the group constituted by the nucleotide sequences SEQ ID No. 1, SEQ ID No. 2, SEQ ID No. 3, SEQ ID No. 4, SEQ ID No. 5, SEQ ID No. 6, SEQ ID No. 7, SEQ ID No. 8.

The invention also proposes a novel strain of *Streptococcus thermophilus* deposited on 26th Feb. 2003 at the Collection Nationale de Cultures de Microorganismes. located at Institut Pastuer, 25 rue du Docteur Roux, F-75724 Paris, France Cedex 15, which is an International Depository Authority, with the accession No. I-2980, under the provisions of the Budapest Treaty; all restrictions upon public access to the deposit will be irrevocably removed upon the grant of a patent on this application; and the deposit will be replaced if viable samples can not be dispensed by the depository.

A subject of the invention is also the nucleotide sequences SEQ ID No. 1, SEQ ID No. 2, SEQ ID No. 3, SEQ ID No. 4, SEQ ID No. 5, SEQ ID No. 6, SEQ ID No. 7, SEQ ID No. 8, as well as a nucleic acid comprising at least one of these nucleotide sequences.

Another subject of the invention is also the plasmids, cloning and/or expression vectors comprising at least one of the nucleotide sequences SEQ ID No. 1, SEQ ID No. 2, SEQ ID No. 3, SEQ ID No. 4, SEQ ID No. 5, SEQ ID No. 6, SEQ ID No. 7, SEQ ID No. 8, as well as a nucleic acid comprising at least one of these nucleotide sequences.

The invention also extends to host bacteria transformed by the plasmids or the vectors described above.

The invention also relates to the process for constructing the strains described above characterized in that these strains are obtained by transformation using a plasmid or vector comprising at least one of the nucleotide sequences SEQ ID No. 1, SEQ ID No. 2, SEQ ID No. 3, SEQ ID No. 4, SEQ ID No. 5, SEQ ID No. 6, SEQ ID No. 7, SEQ ID No. 8, or with a vector comprising a nucleic acid comprising at least one of these nucleotide sequences.

The invention also proposes bacterial compositions comprising at least one strain described above or comprising at least one strain obtained according to the process of the invention.

Finally the invention relates to a food or pharmaceutical composition comprising at least one strain according to the invention or at least one strain obtained according to the process of the invention or the bacterial composition according to the invention.

The present invention has numerous advantages in terms of texturizing the media into which it is incorporated. In particular, it makes it possible to obtain gels from, for example, fermented milks, which are thick, sticky, coating, stringy and resistant to stirring and which are not granular.

Other advantages and characteristics of the invention will become clearly apparent on reading the following description and non-limitative examples given purely by way of illustration.

The invention firstly relates to a strain of lactic bacterium which comprises at least one sequence selected from the group constituted by the nucleotide sequences SEQ ID No. 1, SEQ ID No. 2, SEQ ID No. 3, SEQ ID No. 4, SEQ ID No. 5, SEQ ID No. 6, SEQ ID No. 7, SEQ ID No. 8.

The lactic bacteria are Gram-positive procaryotes which belong to the taxonomic group of the Firmicutes. They are heterotropic and chemo-organotropic; generally anaerobic or aerotolerant, their metabolism can be homo- or hetero-fermentary: the lactic bacteria essentially produce lactic acid by fermentation of a glucidic substrate. Devoid of catalase, the lactic bacteria constitute a heterogeneous group of bacteria in the form of cocci for the genera *Aerococcus, Enterococcus, Lactococcus, Leuconostoc, Oenococcus, Pediococcus, Streptococcus, Tetragenococcus, Vagococcus* and *Weissella*, or in the form of rods for the genera *Lactobacillus* and *Carnobacterium*. The name lactic bacterium is often extended to other related bacteria, such as *Bifidobacterium*.

Among the strains of lactic bacteria which are suitable for the present invention there can be mentioned the genera *Streptococcus, Lactococcus, Lactobacillus, Leuconostoc, Pediococcus* and *Bifidobacterium*.

The preferred strain of lactic bacterium according to the invention is *Streptococcus thermophilus*.

*Streptococcus thermophilus* is a species naturally present in milk and widely used in the food, and in particular dairy, industry because it makes it possible to acidify and texturize the milk. It is a homofermentary thermophilic bacterium.

The invention then relates to the strain of *Streptococcus thermophilus* deposited on 26th Feb. 2003 at the Collection Nationale de Cultures de Microorganismes under number 1-2980.

A subject of the invention is also the nucleotide sequences SEQ ID No. 1, SEQ ID No. 2, SEQ ID No. 3, SEQ ID No. 4, SEQ ID No. 5, SEQ ID No. 6, SEQ ID No. 7, SEQ ID No. 8.

The nucleotide sequences SEQ ID No. 2 to SEQ ID No. 8 form part of an operon of approximately 14,350 base pairs involved in the synthesis of polysaccharides (PS). This operon is included in the sequence SEQ ID No. 1. This means that according to the invention the sequences SEQ ID No. 2 to SEQ ID No. 8 are included in the sequence SEQ ID No. 1.

The structure of the operon according to the invention has been determined (see FIG. 1). Between the genes deoD (upstream of the operon PS) and orfl4.9 (downstream), 17 ORFs (open reading frames) called eps93A, eps13B, eps13C, eps13D, eps13E, eps13F, eps13G, eps13H, eps13I, eps13J, eps13K, eps13L, eps13M, epsl3N, epsf30, epsl3P and IS1193 have been identified. The first 16 ORFs situated on the "sense" strand potentially code for polypeptides involved in the production of the exocellular or capsular polysaccharides; the 17th ORF situated on the "antisense" strand potentially codes for a functional transposase belonging to the family IS1193 (insertion sequence).

It is possible to name each ORF and to position it. The name of each ORF is given below, then secondly the putative function of the derived protein, and finally, thirdly, the position of the region comprising this ORF (in relation to the sequence SEQ ID No. 1 as indicated in the sequence listing):

eps13A: Transcription regulator (342 . . . 1802)
eps13B: Polymerization (chain length regulation) and/or export of the polysaccharides (1803 . . . 2534)
eps13C: Polymerization (chain length regulation) and/or export of the polysaccharides (2543 . . . 3235)
eps13D: Polymerization (chain length regulation) and/or export of the polysaccharides (3245 . . . 3985)
eps13E: Undecaprenyl-phosphate glycosyltransferase (4042 . . . 5409)
eps13F: Undecaprenyl-phosphate glycosyltransferase (5611 . . . 6195)
eps13G: Undecaprenyl-phosphate glycosyltransferase (6251 . . . 6634)
eps13H: Beta-1,4-galactosyltransferase (6643 . . . 7092)
eps13I: Beta-1,4-galactosyltransferase (7092 . . . 7607)
eps13J: Rhamnosyltransferase (7597 . . . 8493)
eps13K: Glycosyltransferase (8763 9797)
eps13L: Repetitive unit polymerase (9827 . . . 10969)
epsl3M: Repetitive unit polymerase (10984 . . . 11793)
eps13N: Glycosyltransferase (11844 . . . 12578)
eps13O: Glycosyltransferase (12633 . . . 13016)
eps13P: Transmembrane transporter (13049 . . . 14482)
IS1193: Transposase (complement (14614.15870)).

The invention also relates to a nucleic acid comprising at least one sequence selected from the group constituted by the nucleotide sequences SEQ ID No. 1, SEQ ID No. 2, SEQ ID No. 3, SEQ ID No. 4, SEQ ID No. 5, SEQ ID No. 6, SEQ ID No. 7, SEQ ID No. 8. By nucleic acid comprising at least one of the sequences listed above is meant, within the meaning of the invention, nucleic acids which comprise at least one ORF the translation product of which has a significant sequence similarity (percentage of identical residues greater than or equal to 80%, after alignment of the sequences for a maximum correspondence between the positions of the residues) with at least one of the polypeptide sequences derived from the ORFs identified in the sequences SEQ ID No. 1 to SEQ ID No. 8.

The nucleotide sequences SEQ ID No. 1, SEQ ID No. 2, SEQ ID No. 3, SEQ ID No. 4, SEQ ID No. 5, SEQ ID No. 6, SEQ ID No. 7, SEQ ID No. 8 can be inserted into a vector by genetic engineering, in particular by recombinant DNA techniques which are widely known to a person skilled in the art.

The invention also relates to a cloning and/or expression vector comprising at least one sequence selected from the group constituted by the nucleotide sequences SEQ ID No. 1, SEQ ID No. 2, SEQ ID No. 3, SEQ ID No. 4, SEQ ID No. 5, SEQ ID No. 6, SEQ ID No. 7, SEQ ID No. 8 or a nucleic acid as defined above.

The preferred vector according to the invention is a plasmid. It can be a replicative or integrative plasmid.

Starting with these vectors and/or plasmids it is possible to transform a bacterium in order to include these vectors and/or plasmids in it. This transformation can be carried out by the technique of electroporation or by conjugation, in a standard manner for a person skilled in the art.

The invention also relates to host bacteria transformed by a plasmid or a vector as defined above.

Preferably, the bacteria transformed are lactic bacteria. In particular, they are lactic bacteria which can be chosen from the genera *Streptococcus, Lactococcus, Lactobacillus, Leuconostoc, Pediococcus* and *Bifidobacterium*.

The preferred strain of lactic bacterium according to the invention is *Streptococcus thermophilus*.

The invention also relates to a process for constructing a strain or transformed host bacterium according to the invention characterized in that they are obtained by transformation using a vector comprising at least one sequence selected from the group constituted by the nucleotide sequences SEQ ID No. 1, SEQ ID No. 2, SEQ ID No. 3, SEQ ID No. 4, SEQ ID No. 5, SEQ ID No. 6, SEQ ID No. 7, SEQ ID No. 8, or with a nucleic acid comprising at least one sequence selected from the group constituted by the nucleotide sequences SEQ ID No. 1, SEQ ID No. 2, SEQ ID No. 3, SEQ ID No. 4, SEQ ID No. 5, SEQ ID No. 6, SEQ ID No. 7, SEQ ID No. 8.

According to the process of the invention, the preferred vector is a plasmid.

Advantageously according to the process of the invention the transformation is followed by an insertion into the genome of the strain or of the host bacterium transformed by at least one recombination event.

The invention also relates to a bacterial composition comprising at least one strain according to the invention or comprising at least one strain obtained according to the process of the invention or comprising at least one bacterium transformed according to the invention By bacterial composition is meant a mixture of different strains, in particular a ferment, or a leaven.

The mixtures of preferred strains according to the invention are mixtures of *Streptococcus thermophilus* with other *Streptococcus thermophilus*, or mixtures of *Streptococcus thermophilus* with *Lactobacillus delbrueckii* subsp. *bulgaricus*, or mixtures of *Streptococcus thermophilus* with other *Lactobacillus* and/or with *Bifidobacterium*, or mixtures of *Streptococcus thermophilus* with *Lactococcus*, or mixtures of *Streptococcus thermophilus* with other strains of lactic bacteria and/or yeasts.

The invention also relates to the use of a strain according to the invention or of a strain obtained according to the process of the invention or of the bacterial composition according to the invention in order to produce a food product or food ingredient.

As preferred food product or food ingredient according to the invention there can be mentioned a dairy product, a meat product, a cereal product, a drink, a foam or a powder.

The invention also relates to a food or pharmaceutical composition comprising at least one strain according to the invention or at least one strain obtained according to the process of the invention or the bacterial composition according to the invention.

A subject of the invention is also a dairy product comprising at least one strain according to the invention or at least one strain obtained according to the process of the invention or the bacterial composition according to the invention.

In the case of the production of a dairy product, the latter is carried out in a manner usual in this field, and in particular by fermentation of a dairy product by incorporation of a strain according to the invention.

As dairy product according to the invention, there can be mentioned a fermented milk, a yogurt, a matured cream, a cheese, a fromage frais, a milk beverage, a dairy product retentate, a process cheese, a cream dessert, a cottage cheese or infant milk.

Preferably the dairy product according to the invention comprises milk of animal and/or plant origin.

As milk of animal origin there can be mentioned cow's, ewe's, goat's or buffalo's milk.

As milk of plant origin there can be mentioned any fermentable substance of plant origin which can be used according to the invention in particular originating from soya seed, rice or malt.

FIG. 1 represents the genetic structure of the PS operon of the strain according to the invention compared with the PS operon of other already known strains of Streptococcus thermophilus.

FIG. 2 represents the factorial design 1-2 of the principal component analysis (PCA) obtained from the sensory data on fermented milks obtained with the different strains of the study.

FIG. 3 represents the means of the scores obtained on the descriptors of TEXTURE ON SPOON for each of the strains of the study. Interpretation of the results of the Newman-Keuls test: the difference between the strains connected by the same letter is not significant.

FIG. 4 represents the means of the scores obtained on the descriptors of TEXTURE IN MOUTH for each of the strains of the study. Interpretation of the results of the Newman-Keuls test: the difference between the strains connected by the same letter is not significant.

Concrete but non-limitative examples of the invention will now be described.

EXAMPLES

1/ Sequencing of the PS Operon of Streptococcus thermophilus CNCM I-2980

The DNA fragment carrying the PS operon of the Streptococcus thermophilus strain CNCM I-2980 was obtained by PCR (polymerase chain reaction) amplification from the genomic DNA extracted from said strain. The amplification was carried out with the Mastercycler thermocycler (Eppendorf) using LA-Taq DNA polymerase (BioWhittaker/Cambrex) and the following primers: 5'-GGGTGMCGTATCT-CAGTMTGGGGACTGG-3' and 5'-CCTGAGTTATGCGACGATTACTTGGCTG-3'. The experimental conditions of this amplification are the following: 14 cycles alternating denaturation at 98° C. for 30 seconds and hybridization-extension at 68° C. for 15 minutes, then 16 cycles alternating denaturation at 98° C. for 30 seconds and hybridization-extension at 68° C. for 15 minutes with an increment of 15 seconds per cycle, then 1 additional extension cycle at 72° C. for 10 minutes. The PCR product was sequenced according to a fragment cloning approach.

2/ Molecular Characterization of the Strain According to the Invention Compared with Already Known Strains of Streptococcus thermophilus Sequence of the PS Operon The sequence of the PS operon of the strain Streptococcus thermophilus CNCM I-2980 was obtained from a DNA fragment of approximately 17,100 base pairs synthesized by PCR in the presence of a purified genomic DNA template of the strain and using two specific primers of preserved genes (deoD coding for a purine-nucleotide phosphorylase, and orf14.9 of unknown function) generally framing the PS operon in the Streptococcus thermophilus described in the literature. The sequence comprised between the genes deoD and orf14.9, corresponding to the sequence SEQ ID No. 1, is given with the sequence listing.

Genetic Organization of the PS Operon

FIG. 1 shows diagrammatically the genetic structure of the PS operon of the strain CNCM I-2980 established by analysis of its nucleotide sequence, as well as the structure of the PS operon of 7 other strains of Streptococcus thermophilus. For the different structures, identified by the name of the strain and by the GENBANK accession number (in parenthesis), the arrows represent the position, size and orientation of the genes from the initiation codon to the stop codon. The significance of the colours and/or units inside the arrows is given by the legend to FIG. 1.

Comparison with the Literature

The structural analysis of the PS operon of the strain CNCM I-2980 shows that it has an overall organization similar to that of the PS operons already known (see FIG. 1); a first ORF potentially involved in the regulation of the transcription of the PS operon, followed by 3 ORFs probably involved in the regulation of the polymerization of the repetitive units of the PS and/or their export, followed by 11 ORFs coding for glycosyltransferases and a polymerase ensuring the assembly of the repetitive unit, themselves followed by 1 ORF potentially involved in the transport of the repetitive units through the plasmid membrane.

The genetic environment of the PS operon of the strain CNCM I-2980 is also similar to that of other known PS operons: upstream the ORF deoD coding for a purine-nucleotide phosphorylase, and downstream in the opposite direction the ORFs IS1193 and orf14.9 respectively coding for a transposase (belonging to the family of the IS1193 insertion sequences, mobile genetic elements) and a protein of unknown function.

However, a sequence comparison carried out between the proteins potentially coded by the ORFs of the operon of the strain CNCM I-2980 and those available in the public databases (GENBANK) show that the genetic content of the PS operon of the strain CNCM I-2980 is novel in its distal part.

The proximal part of the PS operon of Streptococcus thermophilus, and more generally of the streptococci known at present, comprises 4 ORFs called epsA (or cpsA, or capA, or wzg), epsB (or cpsB, or capB, or wzh), epsC (or cpsC, or cpaC, or wzd) and epsD (or cpsD, or capD, or wze) the derived polypeptide products of which, for each of the 4 ORFs, have significant sequence similarities between strains. At this level, the polypeptide products derived from the ORFs eps13A, eps13B, eps13C and eps13D of the PS operon of the strain CNCM I-2980 are not distinguished from those derived from the other PS operons (percentage of identical amino acids greater than or equal to 94%).

Immediately following the ORF epsD, ORF epsE (or cpsE, or capE, or wchA) is present in the majority of the known PS operons in *Streptococcus thermophilus*. In this case also, the sequence similarities are significant between homologous polypeptide products originating from the different known sequences; the translation product of the ORF eps13E of the strain CNCM I-2980 is strongly similar to its homologues originating from other strains.

The organization of the following 4 ORFs (eps13F, eps13G, eps13H and eps13I), of the PS operon of the strain CNCM I-2980, although already described, is less frequent among the different known structures of PS operons of *Streptococcus thermophilus*. This organization is found, sometimes incompletely, in the strains IP6757 (GENBANK accession number AJ289861), "type VII" (GENBANK accession number AF454498) and "type III" (GENBANK accession number AY057915).

In the distal part of the operon, the 7 ORFs eps13J, eps13K, eps13L, eps13M, eps13N, eps13O and eps13P are novel and specific to the PS operon of the strain CNCM I-2980. Although slight, their sequence similarity at protein level, or in certain cases the existence of specific protein units, makes it possible to assign a putative function to the products of these ORFs: potential glycosyl-transferase or polymerase activity for the product of the ORFs eps13J to eps13O, transmembrane transport activity of the PS for the product of the ORF epsl3P.

3/ Comparative Rheology Test of the Strain *Streptococcus thermophilus* CNCM I-2980

The *Streptococcus thermophilus* strains used, CNCM I-2423, CNCM I-2429, CNCM I-2432, CNCM I-2978 and CNCM I-2979 are strains from the Rhodia Food collection. They are for the most part used for the industrial production of fermented milks or yogurts and are recognized for their texturizing properties. They are representative of the strains described in the literature. They are studied hereafter in comparison with the strain CNCM I-2980 and considered as representative of the texturizing strains currently used in the agri-food industry.

The *Streptococcus thermophilus* strains RD736 and RD676 are Rhodia Food industrial strains with a reputation for their low texturizing ability. The polysaccharides which they could produce and their PS operon are not known. They are studied hereafter in comparison with the strain CNCM I-2980 and considered as representative of the non-texturizing strains.

The fermented milk used is obtained by supplementing 100 ml of UHT skimmed milk (Le Petit Vendeen®) with 3% (weight/volume) of skimmed milk powder. The sterility of the solution is obtained by a pasteurization at 90° C. for 10 minutes, the temperature is measured in the core of the milk. The fermentation support thus obtained is inoculated with the strain to be tested at a rate of 10E+6 cfu/ml (colony forming unit/ml) then incubated at 43° C. (in a water bath) until a pH of 4.6 is obtained. The monitoring of the pH is continuously recorded. Fermented milks thus obtained are placed in a ventilated oven at 6° C., until analyzed.

Two types of rheological measurements are carried out: viscosity and flow. The viscosity measurements are carried out at 8° C. on fermented milks, after storage for 1, 7, 14 and 28 days at 6° C. The apparatus used is an RVF-type Brookfield® viscometer (Brookfield Engineering Laboratories, Inc.) mounted on a Helipath stand (Brookfield Engineering Laboratories, Inc.) The viscometer is equipped with a type C needle and the oscillation speed applied to the needle is 10 rpm. The flow measurements are carried out at 8° C. on fermented milks, after storage for 14 days at 6° C. and which have been previously stirred. The apparatus used is an AR1000-N rheometer (TA Instruments) equipped with co-axial cylinders (Radius 1=15 mm, Radius 2=13.83 mm, Height=32 mm, Air gap=2 mm). For the ascending segment, the stress applied in a continuous sweep varies from 0 to 60 Pa for a duration of 1 minute according to a linear mode. For the descending segment, the stress applied in a continuous sweep varies from 60 to 0 Pa for a duration of 1 minute according to a linear mode. The values taken into account are the thixotropic area and the yield point; the latter is calculated according to the Casson model.

The viscosity of the fermented milk obtained with the strain *Streptococcus thermophilus* CNCM I-2980 was measured after storage for 1, 7, 14 and 28 days at 6° C. (Table 1). The viscosity value measured after storage for one day is 53.3 Pa-s. This value varies little over time showing the stability of the fermented milk obtained with the *Streptococcus thermophilus* strain CNCM I-2980. Comparatively (Table 1), the viscosities measured for fermented milks produced with the strains RD736 and RD676, reputed to have a weak texturizing ability, are comprised between 26 and 30 Pa-s. The other strains tested produce fermented milks having lower viscosities than that obtained with the strain CNCM I-2980. It is possible to distinguish one group of strains generating viscosities of the order of 40 Pa·s (CNCM I-2979, CNCM I-2423 and CNCM I-2432) and a second, to which CNCM I-2980 belongs, generating viscosities of the order of 50 Pa·s.

TABLE 1

Viscosity and pH of the fermented milks obtained with the different strains tested, after different storage periods at 6° C.

| | Viscosity in Pa-s/pH | | | |
|---|---|---|---|---|
| Strains | Storage 1 day | Storage 7 days | Storage 14 days | Storage 28 days |
| CNCM I-2980 | 53.3/4.50 | 53.0/4.44 | 53.0/4.42 | 53.5/4.40 |
| CNCM I-2429 | 51.2/4.55 | 51.9/4.45 | 51.0/4.44 | 51.2/4.44 |
| CNCM I-2978 | 50.4/4.56 | 51.8/4.52 | 49.6/4.49 | 51.0/4.45 |
| CNCM I-2432 | 42.4/4.60 | 42.2/4.56 | 43.0/4.55 | 43.0/4.45 |
| CNCM I-2423 | 42.0/4.60 | 41.9/4.40 | 42.0/4.37 | 43.0/4.30 |
| CNCM I-2979 | 37.8/4.54 | 40.7/4.45 | 42.2/4.42 | 42.2/4.33 |
| RD676 | 29.6/4.60 | 30.0/4.57 | 30.0/4.57 | 30.0/4.52 |
| RD736 | 26.0/4.45 | 26.0/4.34 | 28.0/4.34 | 27.0/4.26 |

The flow measurements made it possible to define two significant rheological descriptors (yield point and thixotropic area) for the rheological description of the fermented milks (Table 2). For the fermented milk obtained with the strain CNCM I-2980, the mean values are 5.89 Pa and 488 Pa/s for, respectively, the yield point and the thixotropic area. These values are significantly different from those obtained for the fermented milks obtained with the strains reputed to be non-texturizing (RD676 and RD736). For example for the fermented milk obtained with the strain RD676, these mean values are respectively 17.01 Pa and 17083 Pa/s. In the case of the strains reputed to be texturizing, the yield point and thixotropic area values are much closer to those obtained with the strain CNCM I-2980, but significantly greater however, showing a greater texturizing ability than the strain CNCM I-2980.

TABLE 2

Yield point and thixotropic area values (mean of 3 repetitions) of
fermented milks obtained with the different strains tested after storage
for 14 days at 6° C. measured using the AR1000-N device

| Strains | Yield point (Pa) | Thixotropic area (Pa/s) |
| --- | --- | --- |
| CNCM I-2980 | 5.89 | 488 |
| CNCM I-2429 | 13.32 | 1215 (2 values) |
| CNCM I-2978 | 10.51 | 728 |
| CNCM I-2432 | 12.27 | 1245 |
| CNCM I-2423 | 8.86 | 1344 |
| CNCM I-2979 | 13.56 | 1786 |
| RD676 | 17.01 | 17083 |
| RD736 | 15.91 | 33100 |

4/ Sensory Characterization of the Strain *Streptococcus thermophilus* CNCM I-2980, Comparison with the Reference Strains Fermented milks were evaluated by sensory analysis after storage for 14 days at 6° C. The quantitative descriptive analysis of the fermented milks, maintained at an optimum tasting temperature of 12° C., was carried out by a jury of 9 experts on a non-structured linear scale of 0 to 6 points. This sensory profile analysis was duplicated at an interval of a few days. The judges, selected and trained beforehand, carried out their evaluation on 4 descriptors of texture on a spoon: brittle, resistance to stirring, stringy, granulosity, and on 4 descriptors of texture in the mouth: melting, sticky, thickness, coating. The sensory differences were evaluated by an analysis of variance (called ANOVA) with two factors, a fixed model, followed by a Newman-Keuls mean comparison test with an alpha threshold of 5% on each of the descriptors. A Principal Component Analysis (PCA) with the sensory descriptors as variables and the strains individually was implemented in order to visualize the space produced. An Ascending Hierarchical Classification (AHC) made it possible to isolate the groups of strains on the PCA. The software used for these statistical analyses are Fizz® (Biosystèmes), Statgraphics® and Uniwin plus®.

The fermented milk data obtained with the *Streptococcus thermophilus* strain CNCM I-2980 were compared with those of fermented milks obtained with the other reference strains. The mean values obtained with the different strains for the texture descriptors adopted are indicated in Table 3 and the significant differences emerging from the ANOVA and mean comparison test are listed in Table 4 and FIGS. 3 and 4.

TABLE 3

Mean of the marks allocated by the sensory analysis jury
for fermented milks obtained with the different strains
of the study on the texture descriptors.

| | Descriptors on spoon | | | | Descriptors in mouth | | | |
| --- | --- | --- | --- | --- | --- | --- | --- | --- |
| Strains | Brittle | Resistance to stirring | Granular | Stringy | Melting | Sticky | Thick | Coating |
| CNCM I-2980 | 0.89 | 4.97 | 0.04 | 5.09 | 1.32 | 4.27 | 5.06 | 4.41 |
| CNCM I-2429 | 4.12 | 3.49 | 1.53 | 1.24 | 3.36 | 1.46 | 3.54 | 2.94 |
| CNCM I-2978 | 3.39 | 4.35 | 0.42 | 2.83 | 2.96 | 1.97 | 3.86 | 3.41 |
| CNCM I-2432 | 3.28 | 3.14 | 1.60 | 1.32 | 3.11 | 1.43 | 3.01 | 2.91 |
| CNCM I-2423 | 1.64 | 4.02 | 0.16 | 3.44 | 2.25 | 2.48 | 3.61 | 3.30 |
| CNCM-I 2979 | 3.98 | 2.79 | 2.36 | 0.74 | 3.71 | 0.72 | 2.39 | 2.22 |
| RD676 | 4.98 | 1.46 | 5.14 | 0.17 | 4.98 | 0.04 | 0.91 | 1.03 |
| RD736 | 4.35 | 1.45 | 3.43 | 0.04 | 5.18 | 0.31 | 0.77 | 0.67 |

TABLE 4

Mean comparison on each of the descriptors of texture on a
spoon and texture in the mouth by the Newman-Keuls test at 5%.
Interpretation of the results: the difference between the strains
connected by the same letter is not significant.

| | Descriptors on spoon | | | | Descriptors in mouth | | | |
| --- | --- | --- | --- | --- | --- | --- | --- | --- |
| Strains | Brittle | Resistance to stirring | Granular | Stringy | Melting | Sticky | Thick | Coating |
| CNCM I-2980 | E | A | E | A | D | A | A | A |
| CNCM I-2429 | B | C | D | D | B | C | B | BC |
| CNCM I-2978 | C | B | E | C | B | BC | B | B |
| CNCM I-2432 | C | CD | D | D | B | C | C | BC |
| CNCM I-2423 | D | B | E | B | C | B | B | B |
| CNCM I-2979 | B | D | C | E | B | D | D | C |
| RD676 | A | E | A | F | A | D | E | D |
| RD736 | B | E | B | F | A | D | E | D |

FIGS. 3 and 4 show a histogram representation of the results obtained in Table 4.

For all the descriptors, the strains considered non-texturizing, RD676 and RD736, are significantly differentiated from the other strains. Among the texturizing strains, the strain CNCM I-2980 is clearly and significantly differentiated for all the descriptors, except for granulosity, where it cannot be differentiated from the strains CNCM I-2978 and CNCM I-2423.

The PCA makes it possible to position the strains as a function of their distance in relation to the sensory descriptors.

The design 1-2 of the PCA in FIG. 2 represents 97.3% of the space produced. Component 1 contrasts two groups of sensory variables. The first group, constituted by the variables: resistance to stirring, thickness in the mouth, coating in the mouth, stringy on a spoon and sticky in the mouth, accounts for component 1 on the right. The second group, constituted by the variables: melting in the mouth, brittle on a spoon and granulosity on a spoon, accounts for component 1 on the left. The first group of variables is anti-correlated with the second group. These variables make it possible to analyze the positioning of the strains on this plan. Moreover, the AHC analysis makes it possible to classify the strains in different groups which are represented in the form of dotted circles on the factorial design 1-2.

The factorial design contrasts several groups of strains providing different texture properties. It emerges from these analyses that the strains RD736 and RD676 impart to the fermented milk a brittle and granular texture on a spoon and melting texture in the mouth. In the same manner, they do not produce a thick, sticky or coating texture in the mouth, neither resistant nor stringy on a spoon in comparison with the other groups of strains. They therefore produce a non-texturized fermented milk. By contrast, the strains CNCM I-2429, CNCM I-2432 and CNCM I-2979 produce averagely texturized fermented milks; the strains CNCM I-2423 and CNCM I-2978 produce texturized fermented milks, and the strain CNCM I-2980 produces a highly texturized fermented milk. This analysis shows that the strain CNCM I-2980 provides very particular texture characteristics in fermented milk compared with all of the reference strains.

5/ Comparative Test of Resistance of the *Streptococcus thermophilus* Strain CNCM I-2980 to Phages The sensitivity of a strain to a bacteriophage is established by the lysis plaque method. 100 µl of a culture of the strain to be tested and 100 µl of an appropriate dilution of a serum containing the bacteriophage to be studied are used to seed 5 ml of a M17 glucose agar medium under superfusion (agar 0.6% weight/volume) supplemented at 10 mM with $CaCl_2$. The whole is poured onto the surface of a solidified M17 glucose agar medium (agar 1.5% weight/volume) supplemented at 10 mM with $CaCl_2$. After incubation at 42° C. for 16 hours, the sensitivity of the strain to the bacteriophage is evaluated by the presence of lysis plaques. The absence of a lysis plaque signifies the resistance of this strain to the bacteriophages tested. The sensitivity spectrum of a strain to bacteriophages (also called lysotype) is constituted by all of the sensitivities and resistances to the bacteriophages studied.

Table 5 below defines the bacteriophages used for this study and their strain of origin/propagation. These are strains and phages originating from the Rhodia Food collection. The bacteriophages were selected for their infectiousness vis-à-vis the reference texturizing strains.

TABLE 5

| Phages | |
|---|---|
| Name of the phage | Strain of origin |
| 2972 | CNCM I-2423 |
| 4082 | RD729 |
| 4074 | CNCM I-2429 |
| 4154 | CNCM I-2429 |
| 1272 | CNCM I-2978 |
| 4128 | RD852 |
| 1255 | CNCM I-2432 |
| 1765 | RD728 |
| 4121 | RD862 |

In order to evaluate the industrial benefit of the strain CNCM I-2980 with respect to the problems associated with bacteriophages, the lysotype of the strain CNCM I-2980 was evaluated and compared with those of the reference texturizing strains. Table 6 shows the sensitivities of the strains to these different phages (lysotype) established by the lysis plaque method. It appears that the six strains of the study have different lysotypes. In particular, the strain CNCM I-2980 has a lysotype distinct from that of the other texturizing strains tested. In fact the strain CNCM I-2980 could not be infected by the phages tested.

TABLE 6

| | Lysotype of the strains tested | | | | | |
|---|---|---|---|---|---|---|
| | Strains | | | | | |
| Phages | CNCM I-2980 | CNCM I-2423 | CNCM I-2978 | CNCM I-2432 | CNCM I-2429 | CNCM I-2979 |
| 2972 | − | + | − | − | − | − |
| 4082 | − | + | − | − | − | − |
| 1272 | − | − | + | − | − | − |
| 4128 | − | − | + | − | − | − |
| 1255 | − | − | − | + | − | − |
| 1765 | − | − | − | + | − | − |
| 4074 | − | − | − | − | + | − |
| 4154 | − | − | − | − | + | − |
| 4121 | − | − | − | − | − | + |

+: sensitive to the phage tested;
−: resistant to the phage tested

The invention claimed is:

1. An isolated strain of bacterium comprising at least one sequence selected from the group constituted by the nucleotide sequences SEQ ID No.1, SEQ ID No.2, SEQ ID No.3, SEQ ID No.4, SEQ ID No.5, SEQ ID No.6, SEQ ID No.7, and SEQ ID No. 8.

2. The bacterium according to claim 1 wherein the bacterium is a texturizing strain of lactic bacterium characterized in that it is chosen from the genera *Streptococcus, Lactococcus, Lactobacillus, Leuconostoc, Pediococcus* and *Bifidobacterium*.

3. The bacterium according to claim 1 characterized in that it belongs to the species *Streptococcus thermophilus*.

4. A *Streptococcus thermophilus* deposited on 26th Feb. 2003 at the Collection Nationale de Cultures de Microorganismes under number I-2980.

5. An isolated polynucleotide comprising the sequence as set forth in SEQ ID No. 1.

6. An isolated polynucleotide sequence comprising the sequence SEQ ID No. 2.

7. An isolated polynucleotide sequence comprising the sequence SEQ ID No. 3.

8. An isolated polynucleotide sequence comprising the sequence SEQ ID No. 4.

9. An isolated polynucleotide sequence comprising the sequence SEQ ID No. 5.

10. An isolated polynucleotide sequence comprising the sequence SEQ ID No. 6.

11. An isolated polynucleotide sequence comprising the sequence SEQ ID No. 7.

12. An isolated polynucleotide sequence comprising the sequence SEQ ID No. 8.

13. An isolated polynucleotide comprising at least one sequence selected from the group constituted by the nucleotide sequences SEQ ID No. 1, SEQ ID No.2, SEQ ID No.3, SEQ ID No.4, SEQ ID No.5, SEQ ID No, 6, SEQ ID No.7, and SEQ ID No.8.

14. Cloning and/or expression vector comprising at least one nucleic acid according to claim 13.

15. Vector according to claim 14 characterized in that it is a plasmid.

16. Host bacterium transformed by a vector according to claim 14.

17. Bacterium according to claim 16 characterized in that it is a lactic bacterium.

18. Bacterium according to claim 16 characterized in that it is a lactic bacterium chosen from the genera *Streptococcus, Lactococcus, Lactobacillus, Leuconostoc, Pediococcus* and *Bifidobacterium*.

19. Process for constructing a strain according to claim 1 characterized in that the strain or the bacterium are obtained by transformation using a vector comprising at least one sequence selected from the group constituted by the nucleotide sequences SEQ ID No. 1, SEQ ID No.2, SEQ ID No.3, SEQ ID No.4, SEQ ID No.5, SEQ ID No.6, SEQ ID No.7, SEQ ID NO.8 or a nucleic acid comprising at least one sequence constituted by the nucleotide sequences SEQ ID No. 1, SEQ ID No.2, SEQ ID No.3, SEQ ID No.4, SEQ ID No.5, SEQ ID No, 6, SEQ ID No.7, and SEQ ID No. 8.

20. Process according to claim 19 characterized in that the transformation is followed by an insertion into the genome of the strain or of the host bacterium by at least one recombination event.

21. Process according to claim 19 characterized in that the vector is a plasmid.

22. Bacterial composition comprising at least one strain according to claim 1.

23. Food or pharmaceutical composition comprising at least the strain according to the claim 1.

24. Dairy product comprising at least the strain according to claim 1.

25. Dairy product according to claim 24 characterized in that it is a fermented milk, a yogurt, a matured cream, a cheese, a fromage frais, a milk beverage, a dairy product retentate, a process cheese, a cream dessert, a cottage cheese or infant milk.

26. Dairy product according to claim 24 characterized in that it comprises milk of animal and/or plant origin.

27. Process for constructing a bacterium according to claim 16 characterized in that the strain or the bacterium are obtained by transformation using a vector comprising at least one sequence selected from the group constituted by the nucleotide sequences SEQ ID No. 1, SEQ ID No.2, SEQ ID No.3, SEQ ID No.4, SEQ ID No.5, SEQ ID No.6, SEQ ID No.7, SEQ ID NO.8 or a nucleic acid comprising at least one sequence constituted by the nucleotide sequences SEQ ID No. 1, SEQ ID No.2, SEQ ID No.3, SEQ ID No.4, SEQ ID No.5, SEQ ID No, 6, SEQ ID No.7, and SEQ ID No. 8.

28. Bacterial composition comprising at least one transformed bacterium according to claim 16.

29. Food or pharmaceutical composition comprising the bacterial composition according to claim 22.

30. Dairy product comprising the bacterial composition according to claim 22.

31. A method for fermenting a dairy product comprises using a bacterium culture selected from the group consisting of *Streptococcus, Lactococcus, Lactobacillus, Leuconostoc, Pediococcus* and *Bifidobacterium* containing recombinant DNA comprising at least one sequence selected from the group consisting of the nucleotide sequences SEQ ID No. 1, SEQ ID No.2, SEQ ID No.3, SEQ ID No.4, SEQ ID No.5, SEQ ID No, 6, SEQ ID No.7, and SEQ ID No.8.

32. The method of claim 31 wherein the DNA is in a vector which was used to transform the culture.

33. The bacterial composition of claim 28 wherein the composition is a mixture of strains selected from the group consisting of mixtures of *Streptococcus thermophilus* with other *Streptococcus thermophilus*, mixtures of *Streptococcus thermophilus* with *Lactobacillus delbrueckii subsp. Bulgaricus*, mixtures of *Streptococcus thermophilus* with other *Lactobacillus* and/or with *Bifidobacterium*, mixtures of *Streptococcus thermophilus* with *Lactococcus*, and mixtures of *Streptococcus thermophilus* with other strains of lactic bacteria and yeasts.

34. An isolated strain of bacterium according to claim 1 comprising the nucleotide sequence SEQ ID No.1.

35. An isolated strain of bacterium according to claim 1 comprising the nucleotide sequence SEQ ID No.2.

36. An isolated strain of bacterium according to claim 1 comprising the nucleotide sequence SEQ ID No.3.

37. An isolated strain of bacterium according to claim 1 comprising the nucleotide sequence SEQ ID No.4.

38. An isolated strain of bacterium according to claim 1 comprising the nucleotide sequence SEQ ID No.5.

39. An isolated strain of bacterium according to claim 1 comprising the nucleotide sequence SEQ ID No.6.

40. An isolated strain of bacterium according to claim 1 comprising the nucleotide sequence SEQ ID No.7.

41. An isolated strain of bacterium according to claim 1 comprising the nucleotide sequence SEQ ID No.8.

* * * * *

SEQUENCE LISTING

<160> NUMBER OF SEQ ID NOS: 8

<210> SEQ ID NO 1
<211> LENGTH: 16032
<212> TYPE: DNA
<213> ORGANISM: Streptococcus thermophilus -continued

```
<400> SEQUENCE: 1
tttgtaaaag gacgccattt ggtcgtcctt ttgtgttgta gctaatatct gttcgaagtg       60
ataataagtt aaaattttc aaactactag aaaaaataaa aatatttgga agaagaagac      120
ttttaataaa taggtaaata tctgacaatt taaagtttaa ctactaaaaa tgtgaaagat      180
agttcacaat ataatggaaa atgatataaa ttaaatgatt gatatcataa tgaaaacgtt      240
tttttgtttt ttttgaaaa aaatgacaat tgaaatgaaa ttgtattaat gttacaataa      300
taatggggaa tacttaattt taattttttag gagcaattta tatgagttcg cgtacgaatc      360
gtaagcaaaa acgtacgggt aatagatcat gggggatggt caacgttgga ttgaccattc      420
tgtatgctat tttagcattg gtcttattat tcaccatgtt caattataat ttcctatcct      480
ttaggttttt gaacatcatt atcactattg gtttgttggt agttcttgct attagcatct      540
tccttcagaa gactaagaaa tcaccactag tgacaacggt tgtattggtt atcttctcgc      600
tagtttctct ggttggtatt tttggtttta aacaaatgat tgcatcact aaccgtatga      660 atcagacggc agcatttct gaagtagaaa tgagcatcgt ggttcctaag gaaagtgaca      720
tcaaagatgt gagccagctt actagcgtac aggcacctac taaggttgat aagaacaata      780
tcgagatctt gatgtcagct ctcaaaaaag ataaaaagt tgatgttaaa gttgatgatg      840
ttgcctcata tcaagaagct tatgataatc ttaagtctgg caaatctaaa gctatggtct      900
tgagtgggtc ttatgctagc ctactagagt ctgtcgatag taattatgct tcaaatctaa      960
aaacaattta tacttataaa attaaaaaga agaatagcaa ctctgcaaac caagtagatt     1020
caaaagtctt caatatttat attagtggta ttgataccta cggttcgatt tcaacagtgt     1080
cacgttcaga tgtcaatatt attatgacag taaacatgaa tacacataag attctcttga     1140
cgactactcc acgtgatgca tacgttaaga ttcctggtgg tggagcagac cagtatgata     1200
aattaaccca cgcaggtatt tatggcgttg aaacatctga acaaactctg gaagatctat     1260
atggtactaa gattgattac tatgcccgaa ttaacttcac atctttcctt aagttgattg     1320
accaacttgg tggtgtgaca gtccataatg atcaagcttt cacaagtctt catgggaagt     1380
ttgatttccc agttggagat atccaaatga attcagcaga agcacttgga tttgttcgtg     1440
aacgctatag tttagatggc ggagataatg atcgtggtaa aaaccaggaa aaagtcattt     1500
ctgcgattgt aaacaagttg gcttctctaa agtctgtatc aaactttact tcaatcgtta     1560
ataatctcca agactctgtt cagacaaata tttctttgga taccattaat gctttggcta     1620
atacacaact tgattcaggt tctaaattta cggtgacttc tcaagcagta actggtacag     1680
gttcaaccgg acaattgacc tcttatgcga tgccaaattc tagtctttac atgatgaaac     1740
tagataattc gagtgtggca agtgcctctc aagctatcaa aaatctaatg gaggaaaaat     1800
aagtgattga cgttcactca catattgttt ttgatgttga tgatggtcct aaaactttag     1860
aagaaagttt agatctcatt ggtgaaagtt acgcccaggg ggtacgtaag attgtttcaa     1920
catcccatcg tcgtaagggg atgtttgaga ctccagagga taaaattttt gccaactttt     1980
ctaaggtaaa agcagaagca gaagcacttt atccagactt aactatttat tatgaggtg     2040 aactttatta caccttagac attgtggaga aacttgaaaa gaatctcatt ccgcgcatgc     2100
acaacactca atttgctttg attgagttta gtgctcgcac atcttggaaa gaaattcata     2160
gtgggcttag taatgttttg agagcggggg taacgcctat tgttgctcat attgagcgct     2220
atgatgccct cgaagaaaat gctgaccgtg ttcgagaaat catcaacatg gggtgctata     2280
ctcaagttaa tagctctcat gttctaaaac caaagctctt tggagataaa gataaagtaa     2340
```

-continued

```
gaaaaaaacg tgttcgttat tttttggaga aaaatttggt tcatatggtt gctagcgaca      2400
tgcataatct tgggccgaga ccaccattta tgaaagatgc ttatgaaatt gttaaaaaga      2460
actacggccc caaacgtgct aagaatcttt ttattgaaaa tcccaaaaca ttactagaaa      2520
atcaatattt ataggagata ttatgaatca agataacact aaaagtgatg aaatcgacgt      2580
actagcattg ctacataaac tttggacgaa gaagcttttg attcttttca cagctttta      2640 tttcgctgct ttcagtttct taggtactta tttctttatc caaccaacat atacatcaac      2700
aacgcgtatc tatgttgtta atcaggcaac agataataat aatcttctg ctcaagattt      2760 gcaagctggt acctatttgg caaatgacta taaagagttt attacatcaa atgatgtatt      2820
atcagaagtt attaaagatg aaaaattgaa tttgagtgag gcagaactgt ctaaaatggt      2880
ttcagttaat attcctactg atactcgtct tatttcaatt tctgttaatg ctaaaactgg      2940
tcaagatgcg caaacacttg ctaataaggt tcgtgaagtt gcttcaaaaa aaatcaagaa      3000
ggtgacaaaa gttgaagatg tcacaacgct cgaagaagct aaattgccag agtcaccatc      3060
ttcaccaaat atcaaacgta atgtgcttct tggggcagtg cttggaggat tccttgcagt      3120
ggttggtgta ttggtacgtg aaatcctaga tgatcgtgtt cgccgtccag aagatgtgga      3180
agatgccctt ggaatgacac ttcttggaat tgtccctgat acagataaga tttaaggaga      3240
agaaatgcct ttattaaagt tagttaaatc aaaagtagac tttgctaaaa agacggaaga      3300
gtattataac gctattcgca caaatattca attttctggt gctcagatta aagtgattgc      3360
gattagctct gttgaaactg gtgaaggaaa atcaacgaca tctgttaact ggcgatttc      3420 atttgctagt gttgggctcc gaacacttct gattgatgcg gatacgcgta attctgttt      3480 gtcgggtaca tttaaatcaa atgagcctta taaaggtctt tcaaatttcc tttcaggaaa      3540
tgccgatcta aatgaaacga tttgccaaac tgatatttct ggtttagatg ttattgcatc      3600
tggtcctgta ccacctaatc caacaagtct tttgcaaaat gacaatttta gacatttgat      3660
ggaagttgct cgtagtcgtt atgattatgt tatcatttat acaccaccaa ttggtctggt      3720
cattgatgct ggtattattg cccatcaggc tgatgctagt cttttggtta cagcagctgg      3780
aaaaattaaa cgtcgtttcg taactaaggc ggtcgaacaa ttgaaacaaa gtggttctca      3840
gttcttaggt gtcgtcctta ataaagttga catgacagtt gataaatatg gatcatatgg      3900 ttccttacgga tcatatggtg agtacgggaa aaaacagac caaaagaag gtcattcaag      3960 agcacatcgt cgtagaaaag gatagcatta atggggatga tgcggctcct tataccttaa      4020
cagattaaaa aggggtttag agtgaaagaa aaacaagaaa ttcgtcgcat tgaaattggt      4080
attatacagt tggttgtggt tgttttcgca gccatggtag ctagtaaaat accatataca      4140
gagattaccc aaggaagtat tgtccttta ggtgtcgtac atgtagtgtc ttactatatc      4200
agtagttatt atgaaaatct taagtataga ggctacttgg atgaactcat tgcaactgtc      4260
aaatattgtt tcatatttgc tctaattgca acatttctct cgttttttgc agatggaagt      4320
ttttcaatct cacgtcgcgg acttctttac gtcaccatga tttcaggtgt tctcttatac      4380
gttacaaata ctgttcttaa gtatttccgc tcatctattt atacacgtcg taaaagtaac      4440
aagaatattc tcttgatttc tgatcaggca cgtcttgata tgttttatc tcgtatgaag      4500 gacaatatgg atggtaggat ttcagcagtt tgtgtcttgg ataatcctta tttcactgat      4560
ccatttatca agagtgttaa acctgaaaat ttgattgaat atgcgacaca ctcagtagta      4620
gaccaagttt tgattaatct gccaagtgag cagtacaaga tttgggatta tgcgtcacca      4680
```

-continued

```
tttgaactta tgggaatccc agtatccatt aatttgaatg cccttgaatt tatgagtcag   4740
ggtgaaaaac gtatccaaca attgggtcct ttcaaagttg ttacgttttc tacgcatttt   4800
tatagctatg gagatatctt ggcgaaacgc ttcctcgata tctgtggagc tctagttggt   4860
ttggtgctct gtgggattgt tggaatcttc ctttatccac ttattcgtaa ggatggtggg   4920
ccagccattt ttgctcaaga ccgtgtggga gaaaatggac gtatcttcaa gttttataaa   4980
ttccgttcta tgcgtgttga tgctgaggaa attaaaaagc aattgatgga taaaaatcaa   5040
atgtctggtg gtatgtttaa gatagacaat gatccacgta ttaccaaaat tggacatttc   5100
attcgtaaaa caagtcttga tgaacttcca caattttgga atgttctaaa aggtgatatg   5160
agcttggtag gaacacgtcc accaacattg gatgagtacg aatcttatac accggaacaa   5220
aaacgtcgtt taagttttaa acctggtatc acaggtcttt ggcaagtaag tggacgaagt   5280
gaaattactg attttgatga agttgtaaaa ctagatgttg cttatatgga tgggtggaca   5340
atctggcgag atatcaaaat cttattgaaa acgattaaag tagtagtaat gaaggatgga   5400
gcaaaatgat aacttcaaag atgattagat gagaaaaata atttatattg ttgcttctaa   5460
agggattcct gcaaaatatg gtggatttga gacctttgtt gagaagttga cagagttcca   5520
ataagacaaa gatatccaat attatgtagc ttgtatgcgt gaaaactctg caaaatcagg   5580
aattagagca gatactttat caactgcact gtgcgtagat acaaatatct attccttatg   5640
actgctgaac aacagaagaa tacattagtc attaccacca ctgagagatt gcgattaatg   5700
gaggggctct ttgagtcaga tcaacttcct atcaaatatt tggcaggtat agtagtcatc   5760
ggagatggtg aagtggcgtt tccagaggga gtcccaataa ttccttttga tgatgcgatt   5820
gactttgcga ctcatgaagt tgtcgaccat gtgtttatca acttaccgag tgaacattac   5880
gatctcaaac atcttgtttc cgattttgaa gtcatgggta ttgatgtgag tgtagatatt   5940
aacttatttg atttcagggc tttaaaaaat aaaaaaatca aacaagttgg agaccatagt   6000
atcgtgactt ttaactccaa ttactacaaa catagccata tctttctaaa gcgcatgttg   6060
gatatctttg gggctgtgat tggtcttcta atttgtggtc tggtcgggat tgtcttagct   6120
cctatcattc ggaaagatgg aggaacctgc tattttcgtt cagaaacgag tagggaaaaa   6180
cggtcgtatc tttaattttt ataaattccg ttctatgtat atagatgcag aaaaacggaa   6240
aaaagaactt atggctcaaa accagatgca gggtggtatg tttaaaatgg ataatgaccc   6300
acggattaca ccaattggtc agtttatccg aaaaacaagt ctggatgaat tgccacagtt   6360
ttataatgta ctagttggtg atatgagctt ggtaggtact cgtccaccga cagtggatga   6420
atttgaaaag tatacaccaa gtcaaaaacg acgacttaat tttaaaccgg ggattaccgg   6480
cttatggcaa gttagtgggc gtagcaatat tacggacttt gacgaagtag ttaaactcga   6540
tgttgaatac atagataact ggtcaatttg gtcggatatc aagatattgt tgaagactat   6600
cttcgtagta tttaaaaaag agggaagtaa gtagagtata tcatgaaagt ttgtttagta   6660
ggttcttctg gtgggcattt ggcacacttg aatatgctta aaccttttg gagtgaacag   6720 gaccgctttt gggttacctt tgataaagaa gatgcaagaa gtattttaaa agatgagcag   6780
ttttatccgt gctattttcc tactaacaga aattttaaaa atttagtaaa gaatactttt   6840
ttagcactta aaatttttaag aaaagaaaga cctgacgtta ttatttcatc aggagcagcg   6900
gtagcagttc cgttttttta tcttggtaaa ctgtttggag cgaaaacggt ttatatagaa   6960
gtatttgata gaatagataa accgacagta actgggaaat tggtttatcc agtgacagat   7020
aaatttattg ttcagtggga ggagatgaaa actgtctatc ccaaagctat taatctgggg   7080
```

```
agtattttttt aatgatttttt gttacagtgg gaacccacga acagccctttt aataggctta    7140 ttaaggaagt tgatcgttta aaaaagaag gtattattac agatgaggtt tttattcaga      7200
caggtttttc aacttatgaa cctcaatact gtgactggaa aaacttatc tcttattctg      7260 agatggacaa ctacatgact cactctgata tcattataac ccatggtggt ccagcgacat    7320
tcatgggagc aattgccaaa ggcaaaaaac caattgttgt tccaagacaa gaaaatatg    7380 gagaacatgt aaatgatcat cagttagagt ttgcagaaca ggtttctgga cgttttggga    7440
gtattattgt tgtagaagat attacttcac tctgtgaaat tttattaaaa ggaagtaacg    7500
ttatttgcca aaagcagagt caattttacc ctaaaggatc acagtttatt tttaaattca    7560
aagagatagt tgatgaactt gtagaaggag agattcgtga aacctaaaat acttgtactt    7620
atggcaacct ataatggagg aaaatactta cgagagcaat tagatagtgt ttttttacaa    7680
aaaaatgtgg atattactgt cctggttcgt gacgatggtt caattgacaa tacgtgtgct    7740
attcttgatg aatatagtaa gagatacaac ttaatatggt attcagggca acatctaaat    7800
gttgcgaatg gattttataa tttgatgaa gaagcagtca aatggatttt tgactacttc      7860
gctttctgtg atcaggatga tgtttgggat acagataaac tttccatcgg agtttctgca    7920
atttgtagtt ttaatgaacc tgctttatat tattgtggtc aaagattggc cgacggtaat    7980 ttaaattta tagcaaatca tgaactcaac acagaacgga cactccatac aaggtttatc      8040
ctttctgatt tgctggttg tacaggagtt ttcaataaat cgttattaaa ggaagttgtt      8100
agctatagac cgaagtatat gttgatgcat gatacatgga tattaaaagt ctgtttggct    8160
ctaggtggac aggttattat tgatacaaga ccgcatatgt attataggca acatggtggt    8220
aatacagttg gtcttggaag aagtctatct gcatacttca aacaggtaaa acagtatata    8280
actgaatata aagtggaacc acagatgaag gaacttctct taggatatgg tgatagaatt    8340
atttcggagt atgctgtaat tgcaaatgct tgttgtaatt ataaaacgga tcgtgaggca    8400 cgtactttt tattaaatag aaataatgtt gattttgca cgatgggatt aaatatcacc      8460
tttaaattaa aagttctatt aaataaatta taatttatta ggacgttggt attggaaata    8520
ttttaatatt acctatattc ttattacaat aggaaagtta tttgcgattt taatataaaa    8580
tttgtaggac caatgaaata tttaaaagga accttgctat ttacaatatt aaaagacagc    8640
aatccttaat ttgttaaata atttgctttt tctttgggat tattccaaag aaataagatt    8700
atatttttgt tgttaaaatt ggatatatag taaatttaaa atatcacttt aaaagtaagt    8760
aaatggagga agagtttttg cttttagta ttataatacc tgttttttaat gtcgaaaaat      8820 atcttgagga gtgccttctc tcgattatag ggcagactga tgaaatatct gaaggatgtg    8880
aaataattct tattaatgac gggtcaacag atgatagtgc gaaaatttgt gatgagtatg    8940
agcgaaaata tcctgaattg ataaaggtat tcataggtc aaatcatggt ttgcttctta      9000
cacgaaggtt tggatatcaa catgccgtag gaagatacat aattaattgt gactcagatg    9060
attcgttgga accgattgca cttgaggtgc tcaaagacgc aatcgtcgaa tacaacaacc    9120
cagatgttat tatatttaac cacaatacat ataaaaatgg tgtaaaggag attgcataca    9180
ataacatttt tacagagtct gtttctgccc agatagataa gctagatgtg ttgaaagagt    9240
ttctgactgg aaatcgtatt aatagcgttt gtggtgcaat ttgtaaaaag gattgtattg    9300 atataaaatag agactataat aaatataaag gtcttaataa tggagaagat agccttcaaa    9360
agattgaaca attcaaaagt gcgaacacgt ttgcatatat aaataaacct ctctataatt    9420
```

```
ataggggcagg atcgggtatg accacaaaat tgatcgaaa  ttattttaaa tcttttagaa   9480
tagttctgga tgaaattcaa aaagaacgag aaatgtggga ttttcctgat gtagatagat   9540
atttttcaat taaagttttg tctattgctg gaagagcaat cacacagtca agatacaatt   9600
gttgggagaa taaaagcgag caaataagat acttgcatga tattcgtaat gatgactact   9660
ttaaaaaagc agtgcttcaa ttggctacaa taaggaaata tcttcagaaa gaccatattt   9720
tactaataaa gatgttggat aagggtttga ttcgtcttat agttttgatg ttggatatta   9780
aaaataagat aggctgagtt tgagagggaa agttttaga  ggataaatga atagtataga   9840
taagaagtat cgtattaaac ttgatacgtt aatattttg  attttatta  tgttagcaac   9900
tttcaactat tcgatggagt tatcaatagt tggaaatcca ttcaggcaag tgattcttgt   9960
actgatgctc atattattgt tgtttacaat catccttaag aaatacacaa taaaaaaaat  10020
gattgtattt attacggcta tagtgtatgg attagttaac tatcgagttt caggttatac  10080
agacttattt attttattgc ttgcggcgta tgttgcggat caagtagatt ttaataacgt  10140
gttaaaagtt ctattttggg aaaaattagt gatattttta tcgcttaata tattttcagt  10200
gcttggtgta atagagatga ctaaattctc catcaataag tatctatcca ttgtagaagc  10260
atatgctcca ggatatgttt cttcgaatgt atatggctgc caagcaggag ttttattttt  10320
actttattta tcaattaatc ggtataaatt gacaaagtta aaagttctat tagtttggtt  10380
tttgagtgtt ttagtataca ttatttgtag atcaaggaca gagctaatct tagtatcagt  10440
aacaacagtt cttttattaa tatgtaataa tccaaaaaac tttaataaag ttaagaggat  10500
actctcgtgg ggatatccat ctattttggt tttaaatttt gggttaatat atacttttc   10560
aatactcggt tacggtaatc ccattatgag cactgtaaat gatgtattat tcaatgggag  10620
aattggcttg gctctcatga attttaatac ttatggtatt tcattatttg gctccccaat  10680
tgatgtttcg atagtagcta aaacgaatag atattatgct ttagataatg gttatacagt  10740
tctcgtttta tattacggcc taataggatt attatggtat tcatatattc aaattcagac  10800
tgcaaaaaaa ttagagaaga taaatgagtt ggtcctgatg gttgtactct ttatcatcaa  10860
tatctggggg atttatgaag gaaacatggt ttctttaggt ggaaatttca tgattatagc  10920
ttttctttct aaagtaacag ataattattc agaagaatta aaaagttagt agggagctag  10980
tatatgatac caaaggttat tcactattgt tggtttggag gaaaacctct accagaagat  11040
gcaaaaatgt atatcgagtc atggaaaaaa tatttaccga attatgagat aaaagagtgg  11100
aatgaaacaa actttgattt gaattgttgc gattatgtta aagaggcata tcaagaaaag  11160
aaatgggctt ttgtttcgga ttatgcaaga ctatggatta tttataatta cggtggaatt  11220
tattttgata ctgatgtcga gctaataagt tctcctgaac caatcataga aaatggagct  11280
tttttaggat gtgaactcaa tttcgaaaag gaattatcag gtgatactaa ccaaactgaa  11340
cttgttaacc caggtctagg ttttggtgcg gaaccgaaga aggattttta tcgtgagcta  11400
ttaaatttat acgaatcaca acactttatt gataaaaatg gagacctcaa tttggaaaca  11460
atagtagtga aaacaactag actgttgaag gggcatggtt ttacaggtaa tgattctatt  11520
gaacgagttg caggaattaa tatttactct catgaatatt tttgcccaat taactatcgt  11580
acaggtagaa tttcagtcac tgaaaaaact gtatctatac accattacca agaaagttgg  11640
ctttcggctt tagataagat tattaataag atagaacaga gtagaagtgg agttggaact  11700
cttgaataca aagtcagaag aattgttcct aagccattta gaggagttaa tcgtctgaag  11760
aagaagggaa ttttgggatt tctaaaaaaa tgataagact gtggtattct taataggtct  11820
```

```
cataagttct tcctaatgat ggtttggttg cttttcatta tagttcttat tggacgtttt    11880
gtctgcattc aaaaagctct ataatctcta cagtagtttt acccactata gaaattatag    11940
agccgaaaaa aatactgtcc aaggctaagg tgcctatcaa atcaaaaatg tccatagaag    12000
aagcgtattc gcatttaaat gcttgtagtc cgagacccaa tgggacttgt tatactatga    12060
acaaaataga aaatgcatat gatttgcaaa ttatcattgc ggcctataat accgaacaat    12120
atataaaaga ttgcttgaat tctgtctgtg gtcaacattc aaaatataaa actttggtga    12180
cagttataaa tgatggttca acagatggaa cagagcatat acttgctggt ataacttcgg    12240
aaaatagggg tggaagcgag ctatgcatca gagttataaa tcaggacaac cgagggcttt    12300
cgggtgccag aaatgctgct ctttctaata ttgaagcaaa gtatgtaatg tttttagact    12360
cagatgacat tctcccagag aatactattt ctgttatgtt agataaagca tttataactg    12420
atgcagatat tttacaagaa agttggtatt cgtttgatga tgaaaatgtg agtgaaaaca    12480
ttctggagga aaaagttttt gaagttggaa caaaaggata tgtttcggga tatccttggg    12540
gtaaactata caaagttct gtattaaaaa attttaatt tccaaaagga tactggtttg    12600
aagatacacc aatcactttt attcttgcag caatgccaat taaagtggta accataaagg    12660
atattgttta tggctatcga ctgaatccaa atggaattac agcaaagtca atctttcata    12720
agaaatcagt tgatactttt tgggttacgg aattatgttt gaacgaacta ccaagattca    12780
aagtgtcata tgatcagcaa tcatatgaat atttattaag acaatcattg atgaatgaag    12840
ccaggataaa gaatcaggga aagaaaatac gagaagcagt atttgtcctg acatcagaat    12900
taatgaaaat ttattttagt ggttttctt caaaagattc aaagatgaag aaaatagaaa    12960
tagcacttag aaaatagacaa tttatccagt ttgaattatc aaaactgtat ttgtaatgat    13020
agattaagtg agacagggag aacagttagt gaatagatac agatatttgt taaaaaacat    13080
aggccttttg accctaagta gttttttcaac caaattactt agtttctttt tggtaccgtt    13140
atataccaat atattatcga ctactgaata tggaacctat gatttattta atactacaat    13200
aggtgtatta ctcccgatcc tcacattgaa atacaggaa gcggtgatga gattttccat    13260
tgacagtaag tatgatagaa aatcaatcgt gacagtgaca gcaaggttct ttattctttc    13320
aaatttaatt gttattcttg ggcttttggg aaattataca tttgtattta gcgtgattgc    13380
caagcagtat gccatatttt tcttcctgat gttttatcg cagtcgctat ccgggatgat    13440
aaccatgtat gtcagaggaa tagacaaaat atctgacttg tctttttcaa gtgtaatagc    13500
atctgttatt actatatgct taaatgtttc gttcttagca tttcttcact ggggacttgt    13560
tggatatttt atggccaata taatcggccc gatggttcaa tcactttatt tgattgttaa    13620
agcacatatt ttaggggata ttcatttaga gcaagcatat cagtctgaaa aaaatgaaat    13680
ggttaattat agtaaaccat tgattgcaaa cagcatcgcg tggtgggtaa ataatttttc    13740
tgacagatat atcgttgtga ttttttgtgg gttggctgaa aatggaatat attcagtggc    13800
atcgaaaatt ccttcgatac ttaatatttt tcagacaatt tttaatcagg cgtggacgct    13860
gtctgctgta aaggatttcg accctgagga taaaaacggc ttttcacca atacatataa    13920 agcatataat tgcatgatgg ttgttctatg ctctggaatt attgtattta acaaactgtt    13980
agccagtttt ttgtatgcaa aagactttta tgttgcttgg aaatacgtac catggttaac    14040
aattgcaatc gtattcggag caatgtccgg atatattgga ggaatttttg ctgctgtcaa    14100
ggattctaaa atatttgcga aatcaactgt ttgtggagcg ataactaatg taatattaaa    14160
```

-continued

```
tttaatactt acacccatta tgggaccatt gggagctgct attgctacgg cagtatccta    14220
ttttgaggta tggatttta gatatttgca atccaggaga tatattagga ttagggttaa    14280
tatatttagg gatcttatta cttatttctt gctgttttgt cagtcgatta tactttgat    14340 tgaaatggaa aattcttatt tatatgttct tgaaatcgga attttatttt tgatagtttt    14400
gctatatttt aaggatattc ttttgctatt gaacaaaggt agtaattcaa tcaaaatgaa    14460
gaaaagggga agtgaattat agtatgaaga tagggataat aacgtggttt acaggctcta    14520
attatggcac taaccttcag gcaatcgctc ttcaatatta cttgagaagt cgtggttatg    14580
ggctctttgt caactgtagt gggtgacgaa aagctaacat ctagagagga ccggataggt    14640 cctttttta tgtatgttca gtgtgatgaa gacacgcttc ttaaagttga taaagttct    14700 aaaaccgaag cccaagcgtt tgatgtcttt gatcaactta ttagtcgctt caagtttcgc    14760
gtttgaatag tccgtttcta gtgcgtttt gatgtattgc ttgtgtctaa gaaaagtcct    14820
aaagacagtt tgaaaataat gattgacctt gctcctattt tcctctatca gttcaaagaa    14880
ctcatctact ctcttctcct gaaagtgaaa aaacaaaagc tgataaagtg tatagtagtc    14940
agtaagctct tttgaaaaga ctagtgtctt cgcaacaact tcatgtggtg ctaaagtttg    15000
gcggaaagtc tttgaataaa aagaattgag agatagttta cagctgtcct tttggaagag    15060
tcgccagtga ttttcaagg ctcgataggg tagtgacttc ttatcgaact ggttcatgat    15120
tgcaattctt gtctttaaaa aggcaagtcc aaggtgctgg atgatgtgga aacgatcaag    15180
aacgattttg acgtttggaa agagtctgcg ggctagtggg atataggctc cagacatatc    15240
cattgtgata aactgtacct gttgtcggac tttcaatgga tacttcaaaa agtagtttcg    15300
tatagtagtt tggcggcgat tatcaaggat ggttatgagt tcgtttgtct cataattctg    15360
cgccacaaaa gccaattccc cttcttgaa cccaaactca tcccaggaca taacagcagg    15420
gagtttgtca taatgttcct tgaaagtaaa ctgatcaagc ttacgataga cagtggacgt    15480
cgacacgcga agtcttcttg caatatcagt tagtgacact ttctcagtta ggagttgtgt    15540
aactttttgt cggactagat tggagatttg gcagttttt tcaacgatag atgtctcagc    15600 caccccttact ctcctacaac ttttacactg gaaacgacgt ttttcagac gtagtagagt    15660 tggcgttccc gcttgctcga gaagagagat tttagagttt tttgaaagt cataccttgat    15720 catctttcca tggcaatgag gacatgatgg tgaagggtaa tcaagttttg cttgaatctc    15780
gatatgagtg tcagttttcaa aaacaagtga atcttgata ttttggtctt tgattccgat    15840
taattctgtg ttattcttaa taagtttcat aagttcttcc taatgatggt ttggttgctt    15900
ttcattatag ttcttatggg acttttgtg tacactcaaa aagctctata atccctacag    15960
tagttttacc cactacagaa attatagagc caatatatct cctgtctatt tttatgctac    16020
ttttgggtta gc                                                       16032
```

<210> SEQ ID NO 2
<211> LENGTH: 906
<212> TYPE: DNA
<213> ORGANISM: Streptococcus thermophilus

<400> SEQUENCE: 2

```
aaggagagat tcgtgaaacc taaaatactt gtacttatgg caacctataa tggaggaaaa       60
tacttacgag agcaattaga tagtgttttt ttacaaaaaa atgtggatat tactgtcctg      120
gttcgtgacg atggttcaat tgacaatacg tgtgctattc ttgatgaata tagtaagaga      180
tacaacttaa tatggtattc agggcaacat ctaaatgttg cgaatggatt ttataatttg      240
```

```
atggaagaag cagtcaaaat ggattttgac tacttcgctt tctgtgatca ggatgatgtt    300
tgggatacag ataaactttc catcggagtt tctgcaattt gtagttttaa tgaacctgct    360
ttatattatt gtggtcaaag attggccgac ggtaatttaa attttatagc aaatcatgaa    420
ctcaacacag aacggacact ccatacaagg tttatccttt ctgattttgc tggttgtaca    480
ggagttttca taaatcgtt attaaaggaa gttgttagct atagaccgaa gtatatgttg    540
atgcatgata catggatatt aaaagtctgt ttggctctag gtggacaggt tattattgat    600
acaagaccgc atatgtatta taggcaacat ggtggtaata cagttggtct tggaagaagt    660
ctatctgcat acttcaaaca ggtaaaacag tatataactg aatataaagt ggaaccacag    720
atgaaggaac ttctcttagg atatggtgat agaattattt cggagtatgc tgtaattgca    780
aatgcttgtt gtaattataa aacgatcgt gaggcacgta cttttttatt aaatagaaat    840
aatgttgatt tttgcacgat gggattaaat atcaccttta aattaaaagt tctattaaat    900
aaatta                                                               906

<210> SEQ ID NO 3
<211> LENGTH: 1032
<212> TYPE: DNA
<213> ORGANISM: Streptococcus thermophilus

<400> SEQUENCE: 3
atggaggaag agtttttgct ttttagtatt ataatacctg tttttaatgt cgaaaaatat     60
cttgaggagt gccttctctc gattataggg cagactgatg aaatatctga aggatgtgaa    120
ataattctta ttaatgacgg gtcaacagat gatagtgcga aatttgtga tgagtatgag    180 cgaaaatatc ctgaattgat aaaggtattt cataggtcaa atcatggttt gcttcttaca    240
cgaaggtttg gatatcaaca tgccgtagga agatacataa ttaattgtga ctcagatgat    300
tcgttggaac cgattgcact tgaggtgctc aaagacgcaa tcgtcgaata caacaaccca    360
gatgttatta tatttaacca caatacatat aaaaatggtg taaaggagat tgcatacaat    420
aacattttta cagagtctgt ttctgcccag atagataagc tagatgtgtt gaaagagttt    480
ctgactggaa atcgtattaa tagcgtttgt ggtgcaattt gtaaaaagga ttgtattgat    540
ataaatagag actataataa atataaaggt cttaataatg gagaagatag ccttcaaaag    600
attgaacaat tcaaaagtgc gaacacgttt gcatatataa ataaacctct ctataattat    660
agggcaggat cgggtatgac cacaaaattt gatcgaaatt attttaaatc ttttagaata    720
gttctggatg aaattcaaaa agaacgagaa atgtgggatt ttcctgatgt agatagatat    780
ttttcaatta aagttttgtc tattgctgga agagcaatca cacagtcaag atacaattgt    840
tgggagaata aagcgagca aataagatac ttgcatgata ttcgtaatga tgactacttt    900
aaaaaagcag tgcttcaatt ggctacaata aggaaatatc ttcagaaaga ccatatttta    960
ctaataaaga tgttggataa gggtttgatt cgtcttatag ttttgatgtt ggatattaaa   1020
aataagatag gc                                                      1032

<210> SEQ ID NO 4
<211> LENGTH: 1140
<212> TYPE: DNA
<213> ORGANISM: Streptococcus thermophilus

<400> SEQUENCE: 4
atgaatagta tagataagaa gtatcgtatt aaacttgata cgttaatatt tttgattttt     60
```

-continued

```
attatgttag caactttcaa ctattcgatg gagttatcaa tagttggaaa tccattcagg      120
caagtgattc ttgtactgat gctcatatta ttgttgttta caatcatcct aagaaatac      180 acaataaaaa aaatgattgt atttattacg gctatagtgt atggattagt taactatcga      240
gtttcaggtt atacagactt attttatttta ttgcttgcgg cgtatgttgc ggatcaagta     300
gattttaata acgtgttaaa agttctattt tgggaaaaat tagtgatatt tttatcgctt      360
aatatatttt cagtgcttgg tgtaatagag atgactaaat tctccatcaa taagtatcta     420
tccattgtag aagcatatgc tccaggatat gtttcttcga atgtatatgg ctgccaagca     480
ggagttttat tttacttta tttatcaatt aatcggtata aattgacaaa gttaaaagtt       540
ctattagttt ggttttgag tgttttagta tacattattt gtagatcaag gacagagcta     600
atcttagtat cagtaacaac agttcttta ttaatatgta ataatccaaa aaactttaat     660
aaagttaaga ggatactctc gtggggatat ccatctattt tggttttaaa ttttgggtta     720
atatatactt tttcaatact cggttacggt aatcccatta tgagcactgt aaatgatgta     780
ttattcaatg ggagaattgg cttggctctc atgaattta atacttatgg tatttcatta     840
tttggctccc caattgatgt ttcgatagta gctaaaacga atagatatta tgctttagat     900
aatggttata cagttctcgt tttatattac ggcctaatag gattattatg gtattcatat     960
attcaaattc agactgcaaa aaaattagag aagataaatg agttggtcct gatggttgta    1020
ctctttatca tcaatatctg ggggatttat gaaggaaaca tggtttcttt aggtggaaat    1080
ttcatgatta tagcttttct ttctaaagta acagataatt attcagaaga attaaaaagt    1140
```

<210> SEQ ID NO 5
<211> LENGTH: 810
<212> TYPE: DNA
<213> ORGANISM: Streptococcus thermophilus

<400> SEQUENCE: 5

```
tatatgatac caaaggttat tcactattgt tggtttggag gaaaacctct accagaagat      60
gcaaaaatgt atatcgagtc atggaaaaaa tatttaccga attatgagat aaaagagtgg     120
aatgaaacaa actttgattt gaattgttgc gattatgtta aagaggcata tcaagaaaag     180
aaatgggctt tgtttcgga ttatgcaaga ctatggatta tttataatta cggtggaatt      240 tatttttgata ctgatgtcga gctaataagt tctcctgaac caatcataga aaatggagct    300
tttttaggat gtgaactcaa tttcgaaaag gaattatcag gtgatactaa ccaaactgaa    360
cttgttaacc caggtctagg ttttggtgcg gaaccgaaga aggattttta tcgtgagcta    420
ttaaatttat acgaatcaca acactttatt gataaaaatg gagacctcaa tttggaaaca    480
atagtagtga aaacaactag actgttgaag gggcatggtt ttacaggtaa tgattctatt    540
gaacgagttg caggaattaa tatttactct catgaatatt tttgcccaat taactatcgt    600
acaggtagaa tttcagtcac tgaaaaaact gtatctatac accattacca agaaagttgg    660
ctttcggctt tagataagat tattaataag atagaacaga gtagaagtgg agttggaact    720
cttgaataca aagtcagaag aattgtttct aagccattta gaggagttaa tcgtctgaag    780
aagaagggaa ttttgggatt tctaaaaaaa                                      810
```

<210> SEQ ID NO 6
<211> LENGTH: 750
<212> TYPE: DNA
<213> ORGANISM: Streptococcus thermophilus

<400> SEQUENCE: 6

```
gttcttccta atgatggttt ggttgctttt cattatagtt cttattggac gttttgtctg      60
cattcaaaaa gctctataat ctctacagta gttttaccca ctatagaaat tatagagccg     120
aaaaaaatac tgtccaaggc taaggtgcct atcaaatcaa aaatgtccat agaagaagcg     180
tattcgcatt taaatgcttg tagtccgaga cccaatggga cttgttatac tatgaacaaa     240
atagaaaatg catatgattt gcaaattatc attgcggcct ataataccga acaatatata     300
aaagattgct tgaattctgt ctgtggtcaa cattcaaaat ataaactttt ggtgacagtt     360
ataaatgatg gttcaacaga tggaacagag catatacttg ctggtataac ttcggaaaat     420
aggggtggaa gcgagctatg catcagagtt ataaatcagg acaaccgagg gctttcgggt     480
gccagaaatg ctgctctttc taatattgaa gcaaagtatg taatgttttt agactcagat     540
gacattctcc cagagaatac tatttctgtt atgttagata aagcatttat aactgatgca     600
gatattttac aagaaagttg gtattcgttt gatgatgaaa atgtgagtga aaacattctg     660
gaggaaaaag tttttgaagt tggaacaaaa ggatatgttt cgggatatcc ttggggtaaa     720
ctatacaaaa gttctgtatt aaaaaatttt                                       750

<210> SEQ ID NO 7
<211> LENGTH: 435
<212> TYPE: DNA
<213> ORGANISM: Streptococcus thermophilus

<400> SEQUENCE: 7
tttccaaaag gatactggtt tgaagataca ccaatcactt ttattcttgc agcaatgcca      60
attaaagtgg taaccataaa ggatattgtt tatggctatc gactgaatcc aaatggaatt     120
acagcaaagt caatctttca taagaaatca gttgatactt ttgggttac ggaattatgt     180 ttgaacgaac taccaagatt caaagtgtca tatgatcagc aatcatatga atatttatta     240
agacaatcat tgatgaatga agccaggata aagaatcagg aaagaaaat acgagaagca     300 gtatttgtcc tgacatcaga attaatgaaa atttatttta gtggttttc ttcaaaagat     360 tcaaagatga agaaaataga aatagcactt agaaatagac aatttatcca gtttgaatta     420
tcaaaactgt atttg                                                      435

<210> SEQ ID NO 8
<211> LENGTH: 1452
<212> TYPE: DNA
<213> ORGANISM: Streptococcus thermophilus

<400> SEQUENCE: 8
gtgagacagg gagaacagtt agtgaataga tacagatatt tgttaaaaaa cataggcctt      60
ttgaccctaa gtagtttttc aaccaaatta cttagtttct ttttggtacc gttatatacc     120
aatatattat cgactactga atatggaacc tatgatttat ttaatactac aataggtgta     180
ttactcccga tcctcacatt gaatatacag gaagcggtga tgagattttc cattgacagt     240
aagtatgata gaaaatcaat cgtgacagtg acagcaaggt tctttattct ttcaaattta     300
attgttattc ttgggctttg ggtaaattat acatttgtat ttagcgtgat tgccaagcag     360
tatgccatat ttttcttcct gatgttttta tcgcagtcgc tatccgggat gataaccatg     420
tatgtcagag gaatagacaa aatatctgac ttgtcttttt caagtgtaat agcatctgtt     480
attactatat gcttaaatgt ttcgttctta gcatttcttc actggggact tgttggatat     540
tttatggcca atataatcgg cccgatggtt caatcacttt atttgattgt taagcacat     600
```

-continued

```
attttagggg atattcattt agagcaagca tatcagtctg aaaaaaatga aatggttaat    660
tatagtaaac cattgattgc aaacagcatc gcgtggtggg taaataattt ttctgacaga    720
tatatcgttg tgatttttg tgggttggct gaaaatggaa tatattcagt ggcatcgaaa    780
attccttcga tacttaatat ttttcagaca attttaatc aggcgtggac gctgtctgct    840
gtaaaggatt tcgaccctga ggataaaaac ggcttttca ccaatacata taaagcatat    900
aattgcatga tggttgttct atgctctgga attattgtat ttaacaaact gttagccagt    960
tttttgtatg caaaagactt ttatgttgct tggaaatacg taccatggtt aacaattgca   1020
atcgtattcg gagcaatgtc cggatatatt ggaggaattt ttgctgctgt caaggattct   1080
aaaatatttg cgaaatcaac tgtttgtgga gcgataacta atgtaatatt aaatttaata   1140 cttcaccca ttatgggacc attgggagct gctattgcta cggcagtatc ctatttgag    1200 gtatggattt ttagatattt gcaatccagg agatatatta ggattagggt taatatattt   1260
agggatctta ttacttattt cttgctgttt tgtcagtcga ttatactttt gattgaaatg   1320
gaaaattctt atttatatgt tcttgaaatc ggaatttta ttttgatagt tttgctatat   1380
tttaaggata ttctttgct attgaacaaa ggtagtaatt caatcaaaat gaagaaaagg   1440
ggaagtgaat ta                                                       1452
```